(12) United States Patent
Lovmar et al.

(10) Patent No.: US 8,827,984 B2
(45) Date of Patent: Sep. 9, 2014

(54) URINARY CATHETER

(75) Inventors: Martin Lovmar, Molndal (SE); Niklas Dahlberg, Gothenburg (SE)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/331,525

(22) Filed: Dec. 20, 2011

(65) Prior Publication Data

US 2012/0165791 A1    Jun. 28, 2012

Related U.S. Application Data

(60) Provisional application No. 61/426,061, filed on Dec. 22, 2010.

(30) Foreign Application Priority Data

Dec. 22, 2010 (EP) ................................... 10196626

(51) Int. Cl.
*A61M 27/00* (2006.01)
*A61M 25/00* (2006.01)
*A61M 25/01* (2006.01)

(52) U.S. Cl.
CPC ......... *A61M 25/0021* (2013.01); *A61M 25/007* (2013.01); *A61M 25/0097* (2013.01); *A61M 25/0017* (2013.01); *A61M 25/0068* (2013.01); *A61M 25/0136* (2013.01)
USPC ......................................................... 604/544

(58) Field of Classification Search
CPC .......... A61M 25/007; A61M 25/0097; A61M 25/0017; A61M 25/0068; A61M 25/0136; A61M 25/0021; A61M 25/002; A61M 25/0111; A61F 5/44
USPC .................. 604/4.01–6.01, 6.15, 6.16, 8–10, 604/540–544
See application file for complete search history.

(56) References Cited

U.S. PATENT DOCUMENTS

| | | | |
|---|---|---|---|
| 3,260,258 A | | 7/1966 | Berman |
| 3,630,206 A | * | 12/1971 | Gingold ................... 604/103.08 |
| 4,307,723 A | * | 12/1981 | Finney ............................... 604/8 |
| 5,562,622 A | | 10/1996 | Tihon |
| 6,063,063 A | * | 5/2000 | Harboe et al. ................. 604/256 |
| 2008/0097463 A1 | * | 4/2008 | House ........................... 606/108 |
| 2009/0200187 A1 | * | 8/2009 | Nestenborg et al. .......... 206/364 |

FOREIGN PATENT DOCUMENTS

| | | |
|---|---|---|
| EP | 0217771 B1 | 12/1991 |
| WO | 9426342 A1 | 11/1994 |
| WO | 9641653 A1 | 12/1996 |
| WO | 03002179 A2 | 1/2003 |
| WO | 2004056290 A1 | 7/2004 |
| WO | 2010107900 A2 | 9/2010 |

OTHER PUBLICATIONS

European Search Report, Application No. 10196626.5-1526, Published May 3, 2011.

* cited by examiner

*Primary Examiner* — Philip R Wiest
(74) *Attorney, Agent, or Firm* — Douglas J. Hura; David A. Zdurne; Leana Levin

(57) ABSTRACT

A urinary catheter is disclosed comprising an elongate shaft with an insertion end, a handle connected to the elongate shaft at a distance from the aid insertion end, and a discharge end extending past the handle in a direction opposite the insertion end. The elongate shaft is provided with at least one discharge channel having an elongate opening extending along the elongate shaft, wherein the discharge channel(s), including the elongate opening, further extends at least partly into the discharge end.

18 Claims, 3 Drawing Sheets

URINARY CATHETER

TECHNICAL FIELD OF THE INVENTION

The present invention is related to a urinary catheter comprising an elongate shaft with an insertion end and a handle connected to the elongate shaft at a distance from said insertion end. The catheter is particularly useful for female users.

BACKGROUND

The present invention relates to a urinary catheter for draining urine from the bladder. Urinary catheters are e.g. used by a large group of persons for intermittent catheterization, which is a daily-life procedure, taking place several times a day. Typically catheters for intermittent catheterization are used by patients suffering from urinary incontinence or by disabled individuals like para- or tetraplegics. Using an intermittent catheter, the bladder may be drained through a natural or artificial urethra. Many catheters for intermittent catheterization are provided with a hydrophilic coating or the like, providing a smooth and slippery surface for safe and comfortable insertion in the urinary canal.

To this end, catheters should preferably be designed to enable easy handling and introduction into the urethra, even for users having reduced dexterity. Further, in order to reduce the risk of e.g. urinary tract infections, the catheters should preferably be handled in a clean manner, without directly touching the insertable part of the catheter with the hands, in order to avoid contamination prior to use. Very short catheters, such as catheters intended for female users, may require additional gripping means for enabling easy insertion. Such additional gripping means are e.g. disclosed in WO 96/41653 and WO 94/26342. However, the catheters according to these solutions are structurally relatively complicated, and are costly and cumbersome to produce.

Further, it has been proposed to use a catheter having externally open channels instead of closed lumens, for guiding the urine through the catheter. Such catheters are e.g. disclosed in FIGS. 28-30 of WO 03/002179. However, this type of catheter is still relatively complicated and costly to produce. Further, with this type of catheter, the insertion process is relatively difficult, especially when a short catheter is used. Further, the flow of urine through the channels are difficult to control, and there is a great risk that urine is discharged inadvertently along the channels, thereby resulting in urine being drained uncontrollably, and e.g. spilled where it is not intended to be.

In conclusion there is still a need for catheters, which may be designed for simple and clean use, even for users with a reduced dexterity, and which can be produced in a cost-efficient manner. There is also a need for a catheter which makes use of the urethra in a more natural way.

SUMMARY OF THE INVENTION

There is therefore an object of the present invention to provide a catheter assembly and a method of manufacture that at least partly overcome the above-discussed problems of the prior art.

This object is achieved by means of a catheter assembly and a method and system for manufacture according to the enclosed claims.

According to a first aspect of the invention, there is provided a urinary catheter comprising an elongate shaft with an insertion end, a handle connected to said elongate shaft at a distance from said insertion end, and a discharge end extending past said handle in a direction opposite said insertion end, wherein said elongate shaft is provided with at least one discharge channel having an elongate opening extending along said elongate shaft, said discharge channel(s), including said elongate opening, further extending at least partly into said discharge end.

Hereby, a catheter is obtained which is easy to use and relatively simple to manufacture. For example, the catheter can be injection molded, and since no central lumen and the like is required, the molding becomes relatively simple.

Further, the use of elongate discharge opening(s) along the discharge opening(s) provides contact between the urethra and the discharged urine. This is a great advantage, since it provides a more natural use of the urethra, which e.g. is assumed to reduce the risk of urinary tract infections and the like.

The provision of a handle enables a very convenient use of the catheter, both for insertion and withdrawal of the catheter, and may also function as a stopping means, reducing the risk of inserting the catheter too far into the urethra.

The provision of a discharge end leading the discharge openings past the handle ensures that the urine is discharged in a controlled way, alleviating the risk of spillage, and ensures that the urine does not come into contact with the hand gripping the handle.

Preferably, the discharge end is tapering in a direction away from said handle. This further enhances the controllability of the discharge of urine from the discharge end, and enables a controlled release of urine from the discharge end tip.

The handle may have any form and shape ensuring that it protrudes from the elongate shaft. However, in a preferred embodiment the handle protrudes laterally on one side of the catheter. Hereby, the handle may face upwardly in the use situation, which enables a convenient and easy handling of the catheter. The handle may e.g. be a gripping ring, enabling a ring to be inserted through the ring. Hereby, a firm and easy gripping of the handle is obtained.

It is further preferred that the discharge end is slanted relative to the direction of the elongate shaft, and directed away from said handle. Hereby, the discharge end will be directed downwardly when holding the handle in an upwardly facing position, which further enhances the controlled release of urine from the discharge end.

Preferably, there is provided at least two discharge channels, and preferably at least three discharge channels, said discharge channels being separated around the circumference of the catheter. For example, there may be provided a first discharge channel on a side of the catheter being opposite to the handle, and one discharge channel on each of the sides between said first discharge channel and the side of the catheter on which the handle is provided. Hereby, the channels will all preferably be arranged on or beneath the middle of the catheter when the handle is arranged in an upward direction. This further enhances a controlled release of the discharged urine.

Preferably, the discharge channel(s) extends from the tip portion of the insertion end of the catheter to the end or the vicinity of the end of the discharge end. It is further preferred that the discharge channel(s), including said elongate opening, extends over essentially the entire discharge end.

The present catheter may be of any size suitable for catheterization. However, the catheter is particularly useable for relatively short catheters, intended to be used by females. Hence, it is preferred that the elongate shaft has a length in the range of 5-15 cm, and preferably 7-12 cm, and most preferably about 10 cm. Hereby, a very compact and discrete catheter is obtained, which may easily be carried around by the users.

In order to further facilitate insertion of the catheter, the elongate shaft may comprise a low friction surface, e.g. by being coated with a low-friction material. It is also possible to arrange a hydrophilic material at the surface, said hydrophilic material preferably providing a low-friction character to the catheter surface when wetted. For example, the elongate shaft can be made essentially entirely of a hydrophilic material. Alternatively, the elongate shaft may be provided with a hydrophilic surface coating.

The discharge channels may have any form, and may e.g. have a V-shaped or U-shaped profile. However, in a preferred embodiment, the discharge channels have an average opening width which is narrower than a widest width of said discharge channel. For example, the channels may have a C-shaped cross-section. Hereby, the risk of urine escaping from the channels is minimized. In particular it is preferred that the average opening width is less than ½, and preferably less than ⅓, of the widest width of the discharge channel.

The elongate opening(s) is preferably arranged with a wider opening close to the insertion end, in the part of the catheter arranged to be introduced past the sphincter muscle and into the bladder. Hereby, flow of urine into the discharge channel(s) is facilitated. However, alternatively, the elongate openings may have a similar opening width along the entire elongate shaft.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DETAILED DESCRIPTION OF PREFERRED EMBODIMENTS

Figure 1:
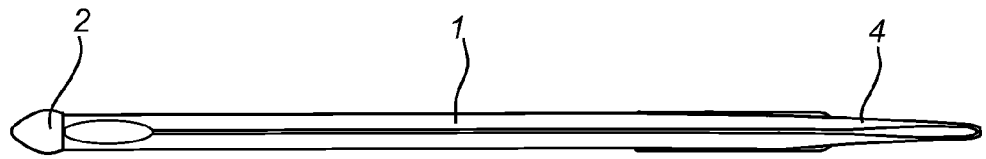
FIG. 1 is a view from beneath of a catheter according to an embodiment of the present invention.
Figure 2:
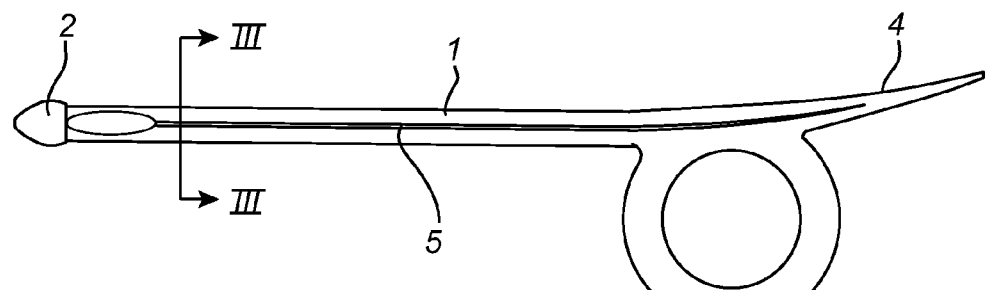
FIG. 2 is a side view of the catheter of FIG. 1.
Figure 3:
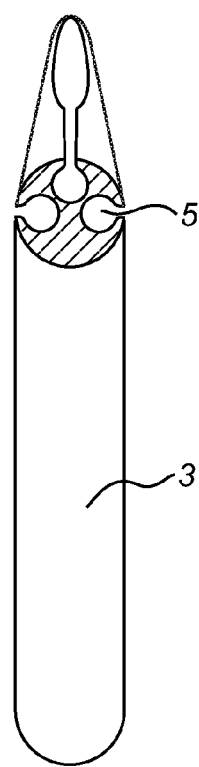
FIG. 3 is a cross-section view of the catheter of FIGS. 1 and 2, in a section along line III-III in FIG. 2.
Figure 4:
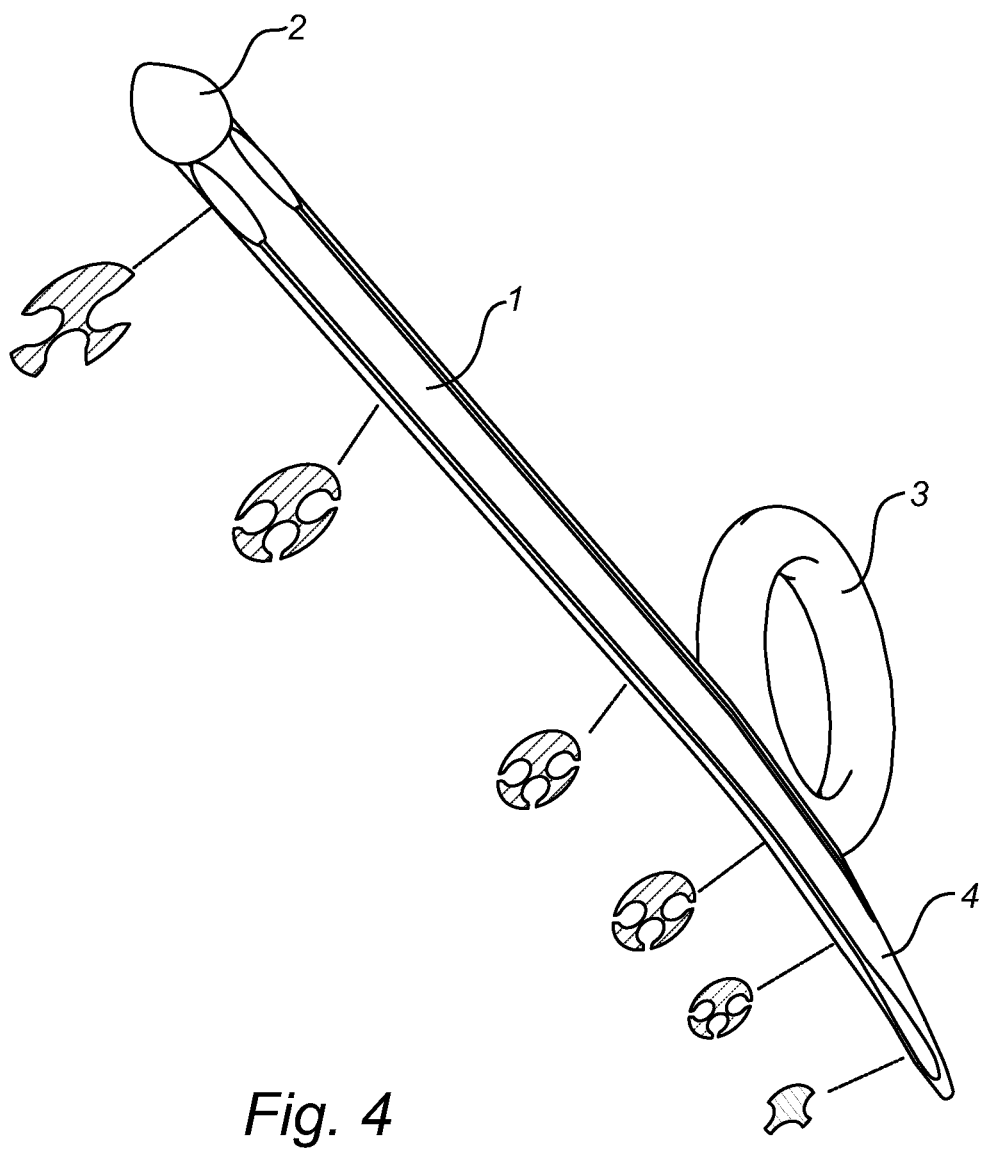
FIG. 4 is a perspective view of the catheter of FIGS. 1-3, and with illustration of the cross-sections at various positions.

In the following detailed description, preferred embodiments of the present invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention.

The following discussion is in particular concerned with the preferred field of use, female urinary catheters, but the catheter may also be used for children and males.

A urinary catheter according to a preferred embodiment is illustrated in FIGS. 1-4. The catheter comprises an elongate shaft 1 with an insertion end 2. The insertion end 2 is preferably provided as a slightly enlarged bulb, with a relatively pointed tip. The insertion end is preferably shaped in the form of an onion, with the tip portion facing forward in the insertion direction.

The catheter further comprises a handle 3 connected to the elongate shaft 1 at a distance from the insertion end 2. The handle may e.g. be in the form of a ring. The handle preferably protrudes laterally on one side of the catheter. Hereby, the handle may face upwardly in the use situation. However, other shapes of the handle are also feasible. For example, the handle may be in the form of a tab, a rod or a plate. It is also possible to provide more than one handle, e.g. protruding in different lateral directions in relation to the elongate shaft. It is also possible to use a handle in the form of e.g. a plate arranged to extend around entire circumference of the elongate shaft.

At the end of the catheter being opposite to the insertion end 2, there is provided a discharge end 4, extending past the handle 3. The discharge end is preferably tapering in a direction away from said handle, so that the cross-sectional dimension of the discharge end diminishes, preferably continuously, towards the tip. Further, the discharge end is preferably slanted relative to the direction of the elongate shaft, and directed away from the handle.

The catheter is further provided with one or several discharge channels 5, extending over the length of the elongate shaft, and at least partly extending into the discharge end. The discharge channels 5 are provided with elongate openings extending along the elongate shaft and extending at least partly into the discharge end. Preferably, the discharge channel(s) extends from the tip portion 2 of the insertion end of the catheter to the end or the vicinity of the end of the discharge end 4. It is further preferred that the discharge channel(s), including said elongate opening, extends over essentially the entire discharge end 4.

Preferably, there is provided at least two discharge channels, and preferably at least three discharge channels, being separated around the circumference of the catheter. In the illustrated example there is provided a first discharge on a side of the catheter being opposite to the handle 3, and one discharge channel on each of the sides between said first discharge channel and the side of the catheter on which the handle is provided. Thus, the two laterally arranged channels are arranged essentially on the middle of the catheter when the handle is arranged in an upward direction, whereas the first discharge channel 51 is arranged at the downward side of the catheter.

The discharge channel(s) may have any form, and may e.g. have a V-shaped or U-shaped profile. However, in a preferred embodiment, as illustrated in the figures, the discharge channels have a C-shaped profile, and thereby have an average opening width which is narrower than a widest width of said discharge channel. In particular it is preferred that the average opening width is less than ½, and preferably less than ⅓, of the widest width of the discharge channel.

Preferably, all the elongate openings have essentially the same opening width. However, it is also feasible to use elongate openings of different widths. For example, an upwardly facing elongate opening may be provided with a greater width then the laterally or downwardly facing elongate opening(s).

Figure 5:
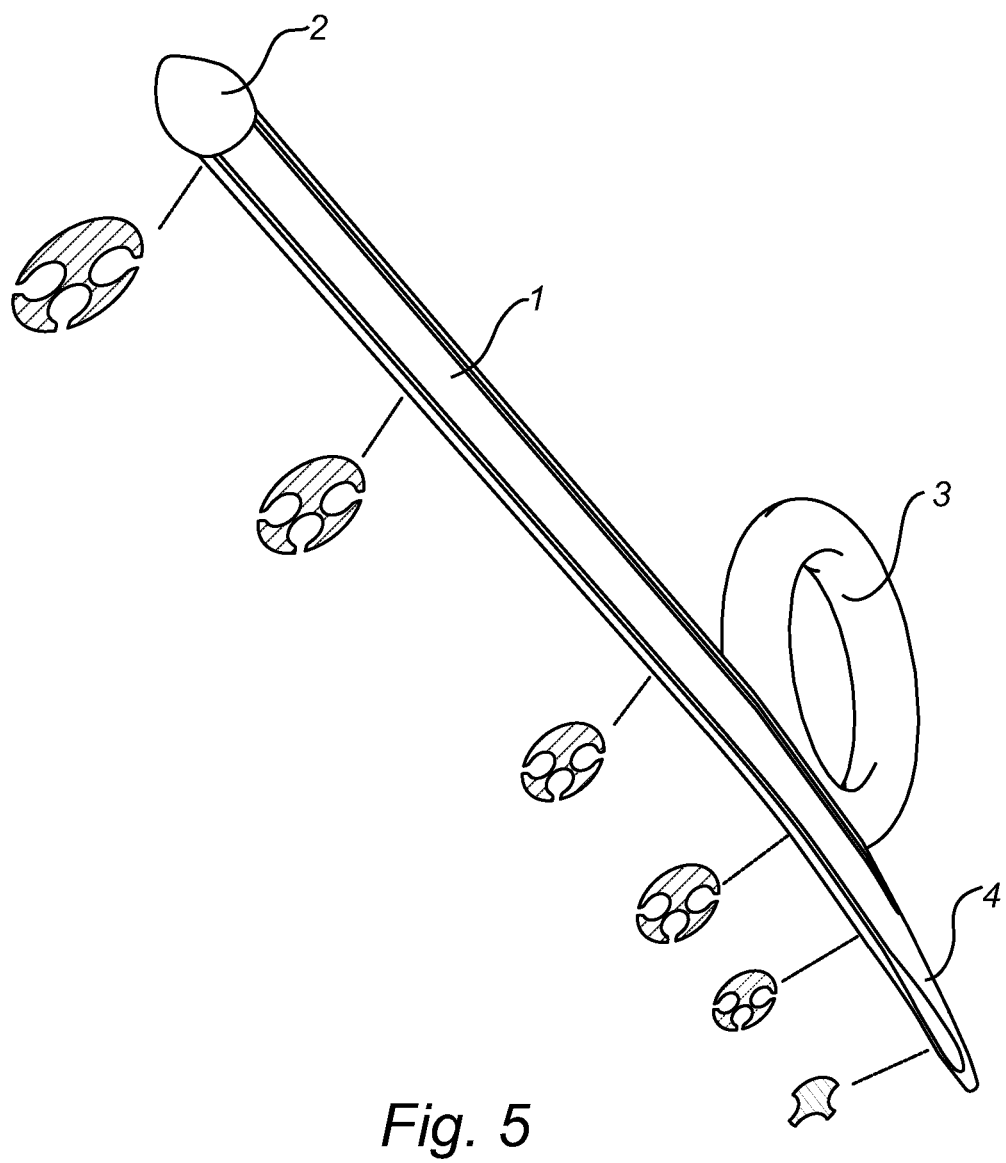
FIG. 5 is a perspective view of a catheter according to an alternative embodiment, and with illustration of the cross-sections at various positions.

It is further preferred that the elongate openings have the same width over a substantial part of the elongate shaft. However, the elongate opening(s) is preferably arranged with a wider opening close to the insertion end, in the part of the catheter arranged to be introduced past the sphincter muscle and into the bladder. Hereby, flow of urine into the discharge channel(s) is facilitated. However, alternatively, the elongate openings may have a similar opening width along the entire elongate shaft, as is illustrated in FIG. 5.

On the discharge end, it is preferred that the opening width gradually increases towards the end of the discharge end, i.e. in a direction away from the handle 3.

The catheter may be of any size suitable for catheterization. However, the catheter preferably presents a relatively short elongate shaft, particularly for use by female users. Hence, it is preferred that the elongate shaft has a length in the range of 5-15 cm, and preferably 7-12 cm, and most preferably about 10 cm. Hereby, a very compact and discrete catheter is obtained. In case the catheter is to be used by male users, the elongate shaft preferably has a length in the range 20-35 cm.

In order to further facilitate insertion of the catheter, the elongate shaft may comprise a hydrophilic material at the surface, said hydrophilic material providing a low-friction character to the catheter surface when wetted. For example, the elongate shaft can be made essentially entirely of a hydrophilic material. Alternatively, the elongate shaft may be provided with a hydrophilic surface coating.

The hydrophilic material may e.g. be polyvinyl pyrrolidone (PVP), but many other types of hydrophilic coatings are known in the art, and may be used in the context of the present invention. The hydrophilic coating provides a low-friction character to the catheter when wetted, thereby facilitating insertion of the catheter into the urethra, and reducing the risk of pain etc.

More specifically, the hydrophilic material may comprise material(s) selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. The preferred hydrophilic polymer is polyvinylpyrrolidone.

In case the hydrophilic material is arranged as a coating, the coating preferably forms a polyurea network, whereby said polyurea network forms a covalent bond to said active hydrogen groups in the substrate. Alternatively, the hydrophilic coating may form an ester bond or an epoxy bond to said active hydrogen groups in the substrate.

The coating may also comprise an osmolality-increasing compound, as is e.g. taught in EP 0 217 771.

The elongate shaft of the catheter is e.g. made of a polymer material, such as polyurethanes, latex rubbers, other rubbers, polyvinylchloride, other vinyl polymers, polyesters, polyether block amid, polypropene, polyethen polyamide and styren-ethen/buten-styren co-polymer and polyacrylates. The elongate shaft can also be made of a polymer blend comprising a polyolefin and a composition having molecules with active hydrogen groups, and preferably a composition having molecules with active hydrogen groups. The polyolefin can comprise at least one polymer selected from the group: polyethene, polypropene, and styrene block copolymer. The composition having molecules with active hydrogen groups can be a polymer having active hydrogen groups bound to the polymer via nitrogen, such as polyamide or polyurethane.

The elongate shaft may also comprise, or substantially consist of, at least one of monosaccharide, disaccharide, oligosaccharide and polysaccharide. In particular, it is possible to use the materials disclosed in co-pending application EP 09171080.6, by the same applicant.

The handle and discharge end are preferably made of the same material as the elongate shaft. However, it is also feasible to at least partly use a different material for the handle and/or the discharge end.

The catheter is preferably injection molded, and since no central lumen and the like is required, the molding becomes relatively simple, and the production lends itself well to automated large scale production.

The catheter has now been disclosed in respect of preferred embodiments. However, many alternatives are feasible, as will be readily appreciated by anyone skilled in the art. For example, the handle may have different shapes and positions, and more than one handle may be provided. Further, the tip portion may have different shapes. For example, the tip portion may be a rounded end of the elongate shaft, without any protruding parts. In such an embodiment, the elongate openings may extend all the way to the very tip of the elongate shaft. Further, the discharge end may have various configurations, such as having different angles relative to the direction of the elongate shaft, or even being in line with the elongate shaft, the tapering may occur continuously over the discharge end, or only be provided at the very end. It is also feasible to use a discharge end without any tapering.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements.

The invention claimed is:

1. A urinary catheter comprising
   an elongate shaft with an insertion end,
   a handle connected to said elongate shaft at a distance from said insertion end, and
   a discharge end extending past said handle in a direction opposite said insertion end,
   wherein said elongate shaft is provided with at least two discharge channels, each of said at least two discharge channels having a discharge opening adjacent the discharge end of the catheter and an elongate opening extending along said elongate shaft, said at least two discharge channels, including said elongate opening, further extending at least partly into said discharge end; and
   wherein said discharge openings have a width that is greater than that of the elongate openings;
   wherein the discharge channels extend from the tip portion of the insertion end of the catheter to the end or the vicinity of the end of the discharge end; and
   wherein said discharge channels being separated around the circumference of the catheter.

2. The urinary catheter of claim 1, wherein the discharge end is tapered and extends in a radial direction from an axis of said elongate shaft and wherein said handle extends in an opposing radial direction from the axis of said elongate shaft relative to said discharge end.

3. The urinary catheter of claim 1, wherein the handle protrudes laterally on one side of the catheter.

4. The urinary catheter of claim 3, wherein the discharge end is slanted relative to the direction of the elongate shaft, and directed away from said handle.

5. The urinary catheter of claim 1, wherein the handle comprises a gripping ring.

6. The urinary catheter of claim 1, wherein the at least two discharge channel, including said elongate opening, extends over substantially the entire discharge end.

7. The urinary catheter of claim 1, wherein the elongate shaft has a length in the range of 5-15 cm.

8. The urinary catheter of claim 1, wherein the elongate shaft comprises a hydrophilic material at the surface, said hydrophilic material providing a low-friction character to the catheter surface when wetted.

9. The urinary catheter of claim 8, wherein the elongate shaft is made essentially entirely of a hydrophilic material.

10. The urinary catheter of claim 8, wherein the elongate shaft comprises a hydrophilic surface coating.

11. The urinary catheter of claim 1, wherein the channels have a C-shaped cross-section.

12. The urinary catheter of claim 1, wherein the average opening width is less than ½ of the widest width of the discharge channel.

13. The urinary catheter of claim 11, wherein the average opening width is less than ⅓ of the widest width of the discharge channel.

14. A urinary catheter comprising
an elongate shaft with an insertion end,
a handle connected to said elongate shaft at a distance from said insertion end, and
a discharge end extending past said handle in a direction opposite said insertion end,
wherein said elongate shaft is provided with at least three discharge channels, each of the at least three discharge channels having an elongate opening extending along said elongate shaft, said at least three discharge channels, including said elongate opening, further extending at least partly into said discharge end;
each of the discharge channels comprising a discharge opening adjacent the discharge end of the catheter, said discharge openings having a width that is greater than that of the elongate openings;
wherein the handle protrudes laterally on one side of the catheter between the at least three discharge channels; and
wherein the discharge end is tapered and extends in a radial direction from an axis of said elongate shaft and wherein said handle extends in an opposing radial direction from the axis of said elongate shaft relative to said discharge end.

15. The urinary catheter of claim 14, wherein the channels have a C-shaped cross-section.

16. The urinary catheter of claim 15, wherein the elongate opening of at least one of the at least three discharge channels has an average opening width which is less than ½ of a widest width of said at least one of said at least three discharge channels.

17. The urinary catheter of claim 14, wherein said at least three discharge channels being separated around the circumference of the catheter; wherein the discharge channels are tapered from the tip portion of the insertion end of the catheter to the end or the vicinity of the end of the discharge end; and wherein the handle protrudes radially between two of the at least three discharge channels.

18. The urinary catheter of claim 14, wherein the elongate shaft has a length in the range of 7-12 cm.

* * * * *